US010941124B2

(12) United States Patent
Meijer et al.

(10) Patent No.: US 10,941,124 B2
(45) Date of Patent: Mar. 9, 2021

(54) DOTA SYNTHESIS

(71) Applicant: GE Healthcare AS, Oslo (NO)

(72) Inventors: Andreas Richard Meijer, Oslo (NO); Arne Wang Aabye, Oslo (NO); Khalid Hussain, Oslo (NO); Sondre Nilsen, Oslo (NO); Mikkel Jacob Thaning, Oslo (NO); Jarle Andre Haugan, Oslo (NO); Ingvil Gausemel, Oslo (NO); Nikolai Enes, Oslo (NO); Silalahi Sumihar, Lindesnes (NO)

(73) Assignee: GE HEALTHCARE AS, Oslo (NO)

( * ) Notice: Subject to any disclaimer, the term of this patent is extended or adjusted under 35 U.S.C. 154(b) by 28 days.

(21) Appl. No.: 16/062,205

(22) PCT Filed: Dec. 19, 2016

(86) PCT No.: PCT/EP2016/081705
§ 371 (c)(1),
(2) Date: Jun. 14, 2018

(87) PCT Pub. No.: WO2017/103258
PCT Pub. Date: Jun. 22, 2017

(65) Prior Publication Data
US 2018/0370925 A1    Dec. 27, 2018

(30) Foreign Application Priority Data
Dec. 18, 2015  (GB) ..................... 1522412

(51) Int. Cl.
*C07D 257/02* (2006.01)
*B01D 9/00* (2006.01)

(52) U.S. Cl.
CPC ......... *C07D 257/02* (2013.01); *B01D 9/0054* (2013.01); *B01D 9/0063* (2013.01)

(58) Field of Classification Search
CPC .................................................. B01D 9/0054
USPC ....................................................... 540/474
See application file for complete search history.

(56) References Cited

U.S. PATENT DOCUMENTS

2009/0216011 A1    8/2009  Axelsson et al.

FOREIGN PATENT DOCUMENTS

| RU | 2405776 C2 | 5/2009 |
|---|---|---|
| RU | 2405776 C2 | 12/2010 |
| WO | 2006112723 A1 | 10/2006 |
| WO | 2013076743 A2 | 5/2013 |
| WO | 2014055504 A1 | 4/2014 |
| WO | 20140555504 A1 | 4/2014 |
| WO | 2014114664 A | 7/2014 |
| WO | 2014114664 A1 | 7/2014 |
| WO | 2015117911 A1 | 8/2015 |
| WO | 2017103258 A1 | 6/2017 |

OTHER PUBLICATIONS

Notification of Transmittal of the International Search Report and the Written Opinion of the International Searching Authority, or the Declaration from International Appl. No. PCT/EP2016/081705, dated Mar. 10, 2017.
Great Britain Search Report from GB Appl. No. GB1522412.4, dated Oct. 25, 2016.
Sorin et al., "Polyaminocarboxylic Acids Rejection by Charged Nanofiltration Membrane," Journal of Membrane Science, Elsevier BV, NL, vol. 279, No. 1-2, Aug. 1, 2006, pp. 446-452.
Russian Office Action and Search Report corresponding to Russian Application No. 2018122071/04, dated Jan. 30, 2020.
Decision to Grant a Patent for an Invention received in Application No. 2018122071/04, dated Jun. 17, 2020, 11 pages. (with translation).

*Primary Examiner* — Ana Z Muresan
(74) *Attorney, Agent, or Firm* — Jeff B. Vockrodt; Culhane Meadows, PLLC

(57) ABSTRACT

The present invention provides methods for the preparation of compounds useful in in vivo therapeutic and diagnostic applications. In particular, the present invention provides a method for the synthesis of 1,4,7,10-tetraazacyclododecane-1,4,7,10-tetraacetic acid (DOTA) and also methods for the preparation of metal chelates of DOTA.

21 Claims, No Drawings

DOTA SYNTHESIS

TECHNICAL FIELD OF THE INVENTION

The present invention relates to the field of magnetic resonance imaging (MRI) and to the synthesis of compounds useful in contrast-enhanced MRI. In particular, the present invention provides a method for the synthesis of 1,4,7,10-tetraazacyclododecane-1,4,7,10-tetraacetic acid (DOTA) and metal chelates thereof.

DESCRIPTION OF RELATED ART 1,4,7,10-tetraazacyclododecane-1,4,7,10-tetraacetic acid (DOTA) is an organic compound consisting of a central 12-membered tetraaza ring of the following structure:

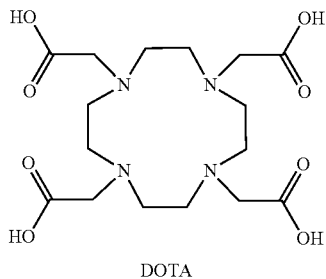 [SMILES: O=C(O)CN1CCN(CC(=O)O)CCN(CC(=O)O)CCN(CC(=O)O)CC1 ; "DOTA"]

DOTA

DOTA is used as a complexing agent, especially for lanthanide ions, and its complexes have medical applications as cancer treatments and in in vivo imaging and diagnosis.

When DOTA is used as part of cancer therapies it typically functions as a chelating agent for the radioisotope $^{90}Y^{3+}$. DOTA can also be conjugated to monoclonal antibodies by attachment of one of the four carboxyl groups as an amide. The remaining three carboxylate anions bind to the yttrium ion. Modified antibody accumulates in tumour cells, concentrating the effects of the radioactivity of $^{90}Y$. Drugs containing this module receive an International Nonproprietary Name ending in "tetraxetan".

DOTA also forms particularly stable chelates with contrast-generating paramagnetic metal ions and especially those that are lanthanide ions. The gadolinium-DOTA chelate (Dotarem®) is one commercially available MRI agent.

The synthesis of DOTA has been extensively described in the literature and there are several synthetic strategies (for example as described by Desreux 1980 Inorganic Chemistry; 19(5): 1319-1324 and by Delgado 1982 Talanta; 29(10): 815-822). The most common DOTA synthesis starts from alkylation of cyclen using a halo-acetic acid and an inorganic base. Chloroacetic acid is the most common alkylation agent and sodium hydroxide is the most common base in the alkylation of cyclen to yield DOTA:

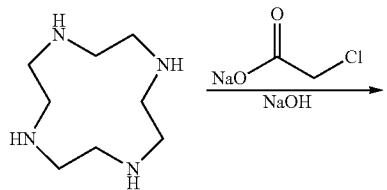

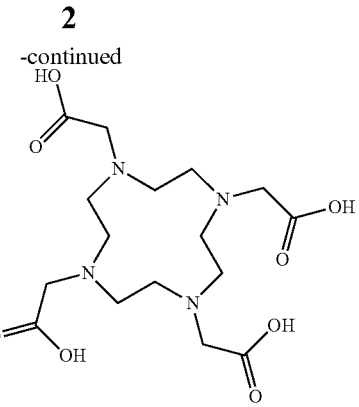

DOTA obtained from this reaction is contaminated with organic impurities and inorganic salts and as a consequence requires purification to be of use in the manufacturing of a pharmaceutical contrast agent. The most common inorganic salt that is present in crude DOTA is sodium chloride. Purification is typically carried out by crystallization of the reaction mixture at a very low pH to obtain DOTA with reduced levels of impurities. A very low pH permits DOTA to be obtained with very low levels of sodium. The chloride impurities are typically removed by purification with ion exchange resin.

EP0998466 B1 (Bracco) describes a DOTA synthetic process including the steps:
1) Synthesis of DOTA from 2a,4a,6a,8a-decahydrotetraazacyclopent[fg]acenaphthylene.
2) Purification by crystallization at pH 2
3) Purification by column purification (PVP)

WO2013076743 (Biophore) describes a DOTA synthetic process consisting of:
1) Purification of DOTA by crystallization from aqueous solvent at pH<0.75.
2) Purification by treatment with anionic ion exchange resin.
3) Precipitation from aqueous solution by addition of organic solvent The above-described processes are of limited use for industrial production of DOTA due to the extremely low pH required for the crystallization step, which would require specialized manufacturing equipment.

Slightly higher pH values have been used in the crystallization process, but still below pH 3. However the DOTA so-obtained is contaminated with substantial amounts of sodium and chloride and subsequent purification with ion exchange resins are required. Some attempts to address this have been described. In WO2014114664 (AGFA) a DOTA synthetic process is taught consisting of:
1) Synthesis of DOTA by alkylation of commercially available cyclen, using a haloacetic acid at a pH>10.
2) Purification by crystallization by acidification to a pH<3, heating/cooling and addition of an organic solvent.
3) Purification of the material obtained in step 2) by adsorption to cationic resin and then desorbing DOTA with a volatile base solution.
4) Purification of the material obtained in step 3) by adsorption to anionic resin and then firstly washing with a dilute organic volatile acid and secondly desorbing DOTA by washing with a concentrated volatile acid.
5) Purification of the material obtained in step 4) by repeated concentrations with water and low boiling water miscible organic solvents.

6) Optional precipitation and filtration of material obtained in 5).

The above process is of limited use for industrial production of DOTA as (i) a low pH is required for the crystallization step and (ii) large amounts of ion exchange resins are required in the subsequent purification steps.

Although crystallization and ion exchange treatment are the most common methods for DOTA purification, nanofiltration has also been suggested as a means to remove impurities. WO2014055504 (Mallinckrodt) describes a DOTA synthetic process consisting of:
1) Synthesis of DOTA from substituted aziridines.
2) Purification by nanofiltration.
3) Purification by crystallization from aqueous solvent at a pH from 1 to 4.

This process suggests a purification strategy based on nanofiltration and crystallization, possibly in combination. There are however no examples demonstrating how efficacious or successful the DOTA purification steps are in comparison with the other processes described hereinabove.

There is therefore still a need for improved methods for removal of organic and inorganic impurities from a crude DOTA reaction mixture utilising technologies and equipment that are suitable for industrial manufacturing.

SUMMARY OF THE INVENTION

In a first aspect the present invention provides a method for the synthesis of 1,4,7,10-tetraazacyclododecane-1,4,7,10-tetraacetic acid (DOTA) wherein said method comprises:
(a) reacting 1,4,7,10-tetraazacyclododecane (cyclen) with a halo-acetic acid and an excess of a base;
(b) crystallising the reaction mixture obtained in step (a) wherein said crystallising is carried out at a pH>3 and <3.5;
(c) filtering an aqueous solution of the crystallised product of step (b) using membrane filtration;
(d) crystallising the filtered solution obtained in step (c).

In a second aspect the present invention provides a method for preparing a metal-DOTA chelate of Formula (I) or Formula (II):

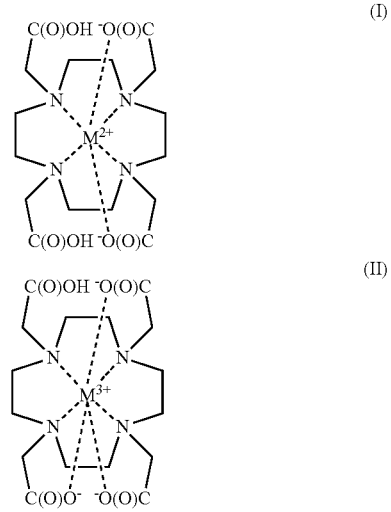

wherein said method comprises treating the product obtained according to the method of the first aspect of the invention with a metal cation, $M^{n+}$, wherein n+ is 2 or 3, provided from a metal ion source selected from the group consisting of metal oxides, metal carbonates, and weak chelates and wherein the metal cation is selected from the group consisting of Gd, Eu, Tb, Dy, Sm, Lu, La, In, Ga, Re, Ru, Fe, Cu, Zn, Ni, Co, Cr, V, Ti, Sc, Zr, Nb, Mo, Rh, Pd, Ag, Cd, Sn, Hf, Ta, W, Os, Ir, Pt, Au and Y, and wherein $M^{2+}$ coordination can occur with any two of the carboxyl moieties.

In a third aspect the present invention provides a method for preparing gadoterate meglumine comprising:
(i) adding $Gd_2O_3$ to the product obtained according to the method of the first aspect of the invention;
(ii) adding meglumine to the complex DOTA-Gd obtained in the step (i).

The methods of the present invention are particularly suitable for industrial manufacturing of DOTA of sufficient purity to be used in pharmaceutical production of contrast agents for MRI. The DOTA obtained by the methods of the present invention is characterised by very low levels of organic and inorganic impurities.

DETAILED DESCRIPTION OF THE PREFERRED EMBODIMENTS

To more clearly and concisely describe and point out the subject matter of the claimed invention, definitions are provided hereinbelow for specific terms used throughout the present specification and claims. Any exemplification of specific terms herein should be considered as a non-limiting example.

The terms "comprising" or "comprises" have their conventional meaning throughout this application and imply that the agent or composition must have the essential features or components listed, but that others may be present in addition. The term 'comprising' includes as a preferred subset "consisting essentially of" which means that the composition has the components listed without other features or components being present.

The term "reacting" as used herein refers to the synthetic reaction between cyclen and a halo-acetic acid to form DOTA. The product of the reacting is a crude reaction mixture comprising DOTA and various impurities.

The term "base" used herein refers to a substance that accepts protons from any proton donor and/or contains completely or partially displaceable OH⁻ ions.

The term "crystallising" refers to a purification method that separates a product from a liquid feedstream either by cooling the feedstream or adding precipitants which lower the solubility of the desired product so that it forms crystals.

The term "filtering" refers to the purification method for the separation of solids from fluids (liquids or gases) by interposing a medium through which only the fluid can pass. The fluid that passes through is called the filtrate. The term "membrane filtration" refers to a method of filtration that separates components of a mixture from the rest of the mixture by permeation through membranes of different pore sizes.

In one embodiment of the method of the invention said halo-acetic acid is selected from the group comprising iodoacetic acid, bromoacetic acid and chloroacetic acid. In one embodiment said halo-acetic acid is chloroacetic acid. In one embodiment said halo-acetic acid is the salt of said halo-acetic acid, e.g. the potassium salt or the sodium salt. In one embodiment said halo-acetic acid is potassium chloroacetate or sodium chloroacetate.

In one embodiment of the method of the invention said base is selected from the group comprising an alkali hydroxide or an alkaline-earth metal hydroxide. In one embodiment said base is an alkali hydroxide. In one embodiment said base is NaOH or KOH. In one embodiment said base is NaOH. In another embodiment of the method of the invention said base is KOH.

In one embodiment of the method of the invention step (a) is carried out at pH 9.0-12.5. In one embodiment said step (a) is carried out at pH 9.5-12.0. In one embodiment said step (a) is carried out at pH 10.0-11.5. In one embodiment said step (a) is carried out at pH 10.5-11.5. In one embodiment said step (a) is carried out at a pH of around 11. The term "pH of around 11" is intended to encompass pH 11 and small variations around pH 11. For example the ranges pH 10.75-11.25, pH 10.8-11.2 and pH 10.9-11.1 can be considered as embodiments of the term "pH of around 11".

In one embodiment of the method of the invention the pH in step (b) is adjusted by addition of an acid selected from the group comprising HCl, $H_2SO_4$, $HNO_3$, HBr, $HClO_4$ and HI. In one embodiment the pH in step (b) is adjusted by addition of HCl. Monitoring and adjusting pH during alkylation and filtration may be carried out manually or in an automated fashion.

In one embodiment of the method of the invention step (b) comprises addition of an organic solvent to the reaction mixture obtained from step (a). In one embodiment said organic solvent is a short-chain alcohol, e.g. ethanol or methanol. In one embodiment said organic solvent is acetone.

In one embodiment of the method of the invention said filtering step (c) is carried out by electrodialysis. The term "electrodialysis" can be understood to be a membrane filtration process during which ions are transported through a semi-permeable membrane under the influence of an electric potential. The membrane can be either cation- or anion-selective such that either positive ions or negative ions selectively flow through.

In another embodiment of the method of the invention said filtering step (c) is carried out by nanofiltration. The term "nanofiltration" as used herein is taken to mean a membrane filtration process whereby the membrane comprises pores of a size suitable for the separation of small molecules and ions from larger (organic) molecules. Typical pore sizes for nanofiltration are in the range generally 1-10 nanometers.

In one embodiment of the method of the invention steps (b), (c) and (d) are independently carried out between pH 3-4, for example at pH 3-3.5 or at pH 3.2.

In one embodiment of the method of the invention step (d) comprises addition of an organic solvent to the reaction mixture obtained from step (c). In one embodiment said organic solvent is a short-chain alcohol, e.g. ethanol, isopropanol or methanol.

In one embodiment the method of the invention comprises:
 (a) reacting 1,4,7,10-tetraazacyclododecane (cyclen) with a halo-acetic acid and an excess of a NaOH at a pH of around 11;
 (b) crystallising the reaction mixture obtained in step (a) wherein said crystallising comprises addition of methanol and is carried out at pH 3-4, e.g. pH 3.2, and wherein the pH is adjusted by addition of HCl;
 (c) filtering an aqueous solution of the crystallised product of step (b) by electrodialysis or by nanofiltration;
 (d) crystallising the filtered solution obtained in step (c) wherein said crystallising comprises addition of methanol and is carried out at pH 3-4, e.g. pH 3.2, and wherein the pH is adjusted by addition of HCl.

Step (a) may be carried out using methods known in the art for example as set out by Desreux (1980 Inorganic Chemistry; 19(5): 1319-1324) and by Delgado (1982 Talanta; 29(10): 815-822).

Crystallisation techniques are well known to those of skill in the art and text books are available describing different methods (see for example "Crystallization: Basic Concepts and Industrial Applications"; 2013 Wiley-VCH: Wolfgang Beckmann, Ed.). Equally, methods for filtration are well known to those of skill in the art and text books are available describing different methods (e.g. "Handbook of Membrane Separations: Chemical, Pharmaceutical, Food and Biotechnological Applications"; 2009 CRC Press: Anil K. Pabby et al, Eds.). Crystallisation and filtration methods most suitable for use in the present invention should meet the requirements for pharmaceutical preparation. Such so-called "good manufacturing practice" (GMP) requirements are readily available from national and regional health authorities (e.g. from the US Food and Drug Administration at http://www.fda.gov/Drugs/GuidanceComplianceRegulatorvInformation/Guidances/ucm064971.htm or from the European Medicines Agency at http://ec.europa.eu/health(documents/eudralex/vol-4/index_en.htm).

Both crystallisation steps of the method of the present invention start with an aqueous solution from the immediate preceding step. Step (a) of reacting cyclen with a halo-acetic acid as defined herein is done in an aqueous solution. Step (c) of filtering is carried out on an aqueous solution that is then concentrated to a particular aqueous concentration prior to step (d).

The pH of each of crystallisation step (b) and filtration step (c) of the method of the invention is important in order to get a good purification and therefore a good yield of DOTA. pH values below 3 or above 3.5 may impact removal of sodium ions, which are mainly removed in steps (b) and (c). In step (c) in order for the positive ion $Na^+$ to cross the membrane a negative ion is required and this is provided in one embodiment as $Cl^-$ in HCl.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

BRIEF DESCRIPTION OF THE EXAMPLES

Example 1 describes a method to obtain DOTA according to a non-limiting embodiment of the invention.

LIST OF ABBREVIATIONS USED IN THE EXAMPLES

DOTA   1,4,7,10-tetraazacyclododecane-1,4,7,10-tetraacetic acid
ICP inductively coupled plasma
MeOH methanol
ppm parts per million

Example 1: Synthesis of DOTA

A modified version of the method of Desreux (1980 Inorganic Chemistry; 19: 1319-1324) was followed.

A 30 L reactor was charged with water (2 L) followed by cyclen (Kinsy China; 1.00 kg, 5.805 mol) followed by more water (1 L), giving a pH 12.4 solution. The pH was monitored throughout using a calibrated pH probe.

A solution of sodium chloroacetate (Sigma-Aldrich, 3.00 kg, 25.3 mol) in water (5 L) was added over a period of 2 hours, together with sodium hydroxide solution (1.839 kg, 22.99 mol; 50% w/w concentration) being added dropwise under manual control, so as to maintain the reaction pH at around pH 11. After the addition was complete, the reaction mixture was stirred for a further 3-4 hours, then cooled to 15° C.

Concentrated hydrochloric acid (35%; ca. 2.57 kg) was added until the pH of the mixture was about pH 3.0. The mixture was allowed to cool to room temperature, then methanol (14 L) added, and the mixture stirred for a further 3 hours. The precipitated crude DOTA was filtered off, and washed with aqueous methanol (1:2 vol/vol; 2×2.35 L). The resulting cake was dried using suction, giving a white powder (2.44 kg; 90% yield). The material was analysed by ICP-analysis and Karl Fischer titration, indicating a purity of 87% (remaining content water and ca. 2.5% by weight of sodium). Methanol content was assessed by GC.

The above crude DOTA was dissolved in water and subjected to nanofiltration, whereby the sodium content was reduced from 2.5 w % to 1.3 w %. An aqueous solution of this reduced salt DOTA was dissolved in water, the solution concentrated and then methanol added to induce crystallisation and remove the remaining sodium chloride. The isolated crystals had a much lower sodium content (0.0-0.3 w %,), with ca. 4 w % methanol.

The following table summarises the nature of the reaction mixture following each step:

| | Na (w/w %) | MeOH (w/w %) | Water (w/w %) | DOTA (w/w %) |
|---|---|---|---|---|
| Reaction | 25 | — | solution | 54 |
| $1^{st}$ crystallization | 7-15 | <1 | — | — |
| Nanofiltration | <1.3 | — | solution | — |
| $2^{nd}$ crystallization | <50 ppm | 4.5 | 4.5 | 90 |

Example 2: Lame-Scale Synthesis of DOTA

A 6000 L reactor was charged with water (360 L) followed by cyclen (Kinsy, Spain; 180 kg, 1.045 kmol).

A solution of sodium chloroacetate (Akzo Nobel, 540 kg, 4.55 kmol) in water (900 L) was added over a period of 1.5 hours, together with sodium hydroxide solution (377 kg 50% w/w concentration; 4.71 kmol NaOH;) being added continuously to maintain the reaction pH at around pH 11. After the addition was complete, the reaction mixture was stirred for a further 5 hours.

Concentrated hydrochloric acid (35%; ca. 462 kg) was added until the pH of the mixture was about pH 3.2. Then methanol was added (2340 L) at ca. 55° C. and cooled to 10° C., cooling rate ca. 5° C. per hour.

The precipitated crude DOTA was filtered off, and washed with aqueous methanol (1:2 vol/vol; 4×315 L). The resulting cake was dried in the filter using reduced pressure and heating (55° C. jacket temperature).

The above crude DOTA was dissolved in water and sampled for measurement of quantity and sodium content (369 kg DOTA; 87% yield; 5.26% Na) and subjected to nanofiltration whereby the sodium content was reduced from 5.26 w % to 0.84 w %. The aqueous solution this reduced salt DOTA was concentrated and then methanol added to induce crystallization and remove the remaining sodium chloride. The isolated crystals had a sodium content NMT 10 µg/g DOTA.

The invention claimed is:

1. A method for the synthesis of 1,4,7,10-tetraazacyclododecane-1,4,7,10-tetraacetic acid (DOTA), the method comprising:
    (a) reacting 1,4,7,10-tetraazacyclododecane (cyclen) with a halo-acetic acid and an excess of a base;
    (b) crystalizing the reaction mixture obtained in step (a) wherein said crystalizing the reaction mixture obtained in step (a) is carried out at a pH>3 and <3.5 in an organic solvent;
    (c) filtering an aqueous solution of the crystallized product of step (b) using membrane filtration; and
    (d) crystalizing the filtered solution obtained in step (c) wherein said crystalizing the reaction mixture obtained in step (a) is carried out at a pH>3 and <3.5, wherein the sodium content of the resulting DOTA is <50 ppm.

2. The method of claim 1, wherein said halo-acetic acid is selected from iodoacetic acid, bromoacetic acid or chloroacetic acid.

3. The method of claim 1, wherein said halo-acetic acid is chloroacetic acid.

4. The method of claim 1, wherein said halo-acetic acid is the salt of said halo-acetic acid.

5. The method of claim 1, wherein said base is selected from an alkali hydroxide or an alkaline-earth metal hydroxide.

6. The method of claim 1, wherein the pH in step (b) is adjusted by addition of an acid selected from HCl, $H_2SO_4$, $HNO_3$, HBr, $HClO_4$ and HI.

7. The method of claim 1, wherein the pH in step (b) is adjusted by addition of HCl.

8. The method of claim 1, wherein said organic solvent is ethanol, isopropanol or methanol.

9. The method of claim 1, wherein said filtering step (c) is carried out by membrane filtration.

10. The method of claim 1, wherein said filtering step (c) is carried out by nanofiltration.

11. The method of claim 1, wherein each of steps (b), (c) and (d) is independently carried out at pH 3-3.5.

12. The method of claim 1, wherein each of steps (b), (c) and (d) is independently carried out at pH 3.2.

13. The method of claim 1, wherein said organic solvent is ethanol or methanol.

14. A method for the synthesis of 1,4,7,10-tetraazacyclododecane-1,4,7,10-tetraacetic acid (DOTA), the method comprising:
    (a) reacting 1,4,7,10-tetraazacyclododecane (cyclen) with a halo-acetic acid and an excess of a NaOH at a pH of around 11;
    (b) crystalizing the reaction mixture obtained in step (a) wherein said crystalizing comprises addition of methanol and is carried out at pH 3.2-4 and wherein the pH is adjusted by addition of HCl;
    (c) filtering an aqueous solution of the crystallized product of step (b) by membrane filtration or by nanofiltration; and (d) crystallizing the filtered solution obtained in step (c) wherein said crystallizing comprises addition of methanol and is carried out at pH 3.2-4, and wherein the pH is adjusted by addition of HCl, wherein the sodium content of the resulting DOTA is <50 ppm.

15. A method for preparing a metal-DOTA chelate of Formula (I) or Formula (II):

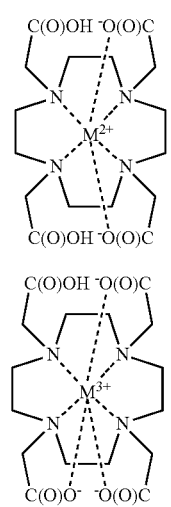

the method comprising,
treating the product obtained according to the method of claim 1 with a metal cation, $M^{n+}$,
wherein n+ is 2 or 3, provided from a metal ion source selected from metal oxides, metal carbonates, or weak chelates and wherein the metal cation is selected from Gd, Eu, Tb, Dy, Sm, Lu, La, In, Ga, Re, Ru, Fe, Cu, Zn, Ni, Co, Cr, V, Ti Sc, Zr, Nb, Mo, Rh, Pd, Ag, Cd, Sn, Hf, Ta, W, Os, Ir, Pt, Au or Y, and wherein $M^{2+}$ coordination can occur with any two of the carboxyl moieties.

16. The method of claim 15, wherein said metal cation is Gd.

17. The method of claim 16, wherein metal ion source is $Gd_2O_3$ and the compound Formula (II) is gadoterate meglumine.

18. A method for preparing gadoterate meglumine, the method comprising:
(i) adding $Gd_2O_3$ to the product obtained according to the method defined in claim 1; and
(ii) adding meglumine to the complex DOTA-Gd obtained in the step (i).

19. The method of claim 1, wherein said organic solvent is methanol.

20. The method of claim 1, wherein each of steps (b), (c) and (d) is independently carried out at pH 3.2-3.5.

21. The method of claim 20, wherein said organic solvent is methanol.

* * * * *